United States Patent [19]

Rieser

[11] 4,425,909
[45] Jan. 17, 1984

[54] LARYNGOSCOPE

[76] Inventor: Michael J. Rieser, 525 W. Earll, No. 318, Phoenix, Ariz. 85013

[21] Appl. No.: 336,697

[22] Filed: Jan. 4, 1982

[51] Int. Cl.³ .............................................. A61B 1/26
[52] U.S. Cl. ...................................... 128/16; 128/11; 128/13
[58] Field of Search ................................... 128/10-19, 128/3

[56] References Cited

U.S. PATENT DOCUMENTS

| | | | |
|---|---|---|---|
| 1,344,020 | 6/1920 | Bugbee | 128/15 |
| 2,289,226 | 7/1942 | Von Foregger | 128/11 |
| 2,648,329 | 8/1953 | Morch | 128/11 |
| 3,550,584 | 12/1970 | Ring | 128/12 |
| 3,884,222 | 5/1975 | Moore | 128/11 |
| 4,112,933 | 9/1978 | Moses | 128/15 X |
| 4,320,745 | 3/1982 | Bhitiyakul et al. | 128/16 X |
| 4,337,761 | 7/1982 | Upsher | 128/16 X |

Primary Examiner—Lee S. Cohen
Assistant Examiner—Angela D. Sykes
Attorney, Agent, or Firm—Drummond & Nissle

[57] ABSTRACT

An improved laryngeal speculum for examining the throat and larynx of a patient. The speculum includes an elongate blade, an elongate handle and a neck interconnecting the blade and handle. The longitudinal axis of the handle is generally perpendicular to the longitudinal axis of the blade. The neck is shaped, contoured, and dimensioned such that when the blade is positioned inside the mouth and throat of a patient and a lifting force is exerted on the handle parallel to the longitudinal axis thereof, torque forces on the handle and blade generally will not occur as a result of the blade being pressed against the mouth and throat of the patient during the application of the lifting force.

2 Claims, 4 Drawing Figures

U.S. Patent  Jan. 17, 1984  4,425,909
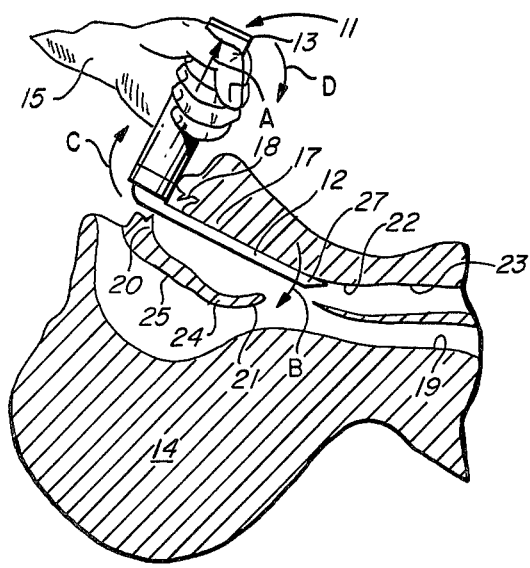
FIG-1
(PRIOR ART)
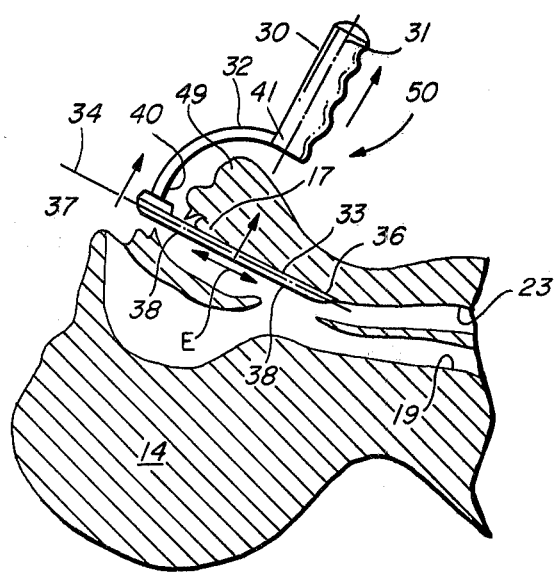
FIG-2
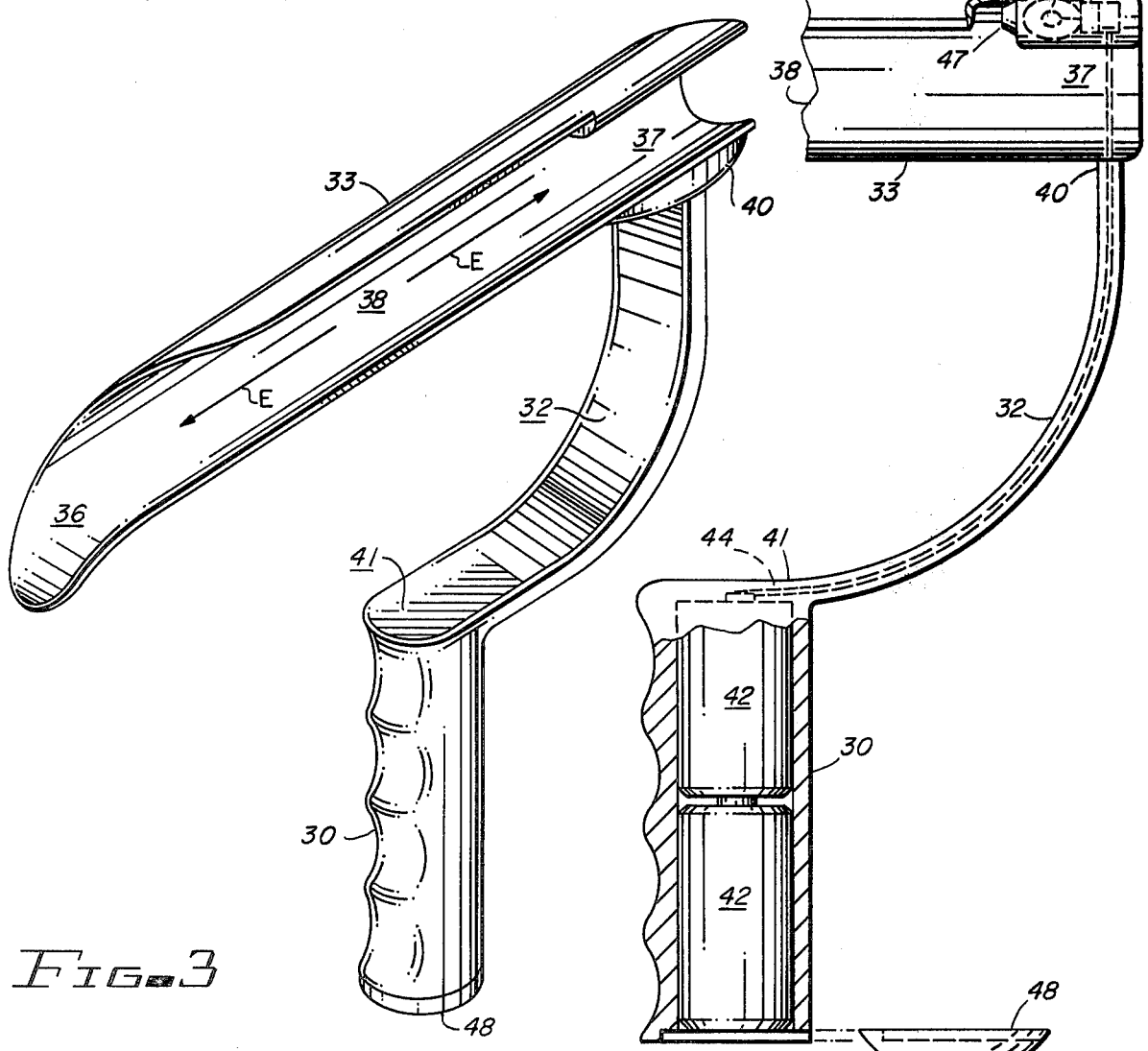
FIG-3
FIG-4

LARYNGOSCOPE

This invention relates to medical and surgical instruments.

More particularly, the invention pertains to laryngoscopes including a shaped, elongate blade inserted in the mouth and throat of a patient and an elongate handle positioned outside the mouth of the patient and connected and generally perpendicular to one end of the blade, the handle being grasped and lifted away from the patient to force the length of the blade against the tongue and throat of a patient to expand and open the mouth and throat for viewing and intubation.

In a further and more specific respect the invention pertains to a laryngeal speculum in which torque forces on the handle and blade do not occur when the blade is inserted in the mouth and throat of a supine patient and the handle is grasped and pulled upwardly away from the patient.

Laryngeal speculums or laryngoscopes are well known in the art. See for example U.S. Pat. Nos. 2,289,226 to Foregger and 2,648,329 to Morch. As illustrated in these patents a conventional laryngoscope is L-shaped and includes an elongate blade which is inserted in the mouth and throat of a patient and includes an elongate handle attached to one end of the blade. The handle is generally perpendicular to or at least laterally disposed with respect to the blade.

In emergency situations or during the practice of various surgical procedures on a supine patient the free end of the laryngoscope blade is inserted in the mouth and throat of the patient and the handle, which is positioned outside the mouth of the patient, is grasped and lifted upwardly away from the patient in a direction parallel to the position of the longitudinal axis of the handle when the laryngoscope is initially properly positioned in the patient's mouth. The longitudinal axis of the speculum handle is generally perpendicular to the longitudinal axis of the blade.

When the laryngoscope handle is lifted away from a patient, the length of the blade positioned in the patient's mouth bears against tongue and throat areas and expands and opens the mouth for viewing by the medical attendant utilizing the laryngoscope. It is very important that the handle be lifted in a direction parallel to the position of the longitudinal axis thereof and not rotate. If the handle and blade rotate about an imaginary axis perpendicular to the plane defined by the longitudinal axes of the blade and handle, the tip of the blade positioned in the throat of the patient will move to a position which will not properly expose inner throat structures for viewing by the attendant.

During utilization of a laryngoscope the patient is normally supine and the medical attendant handling the laryngoscope is positioned behind the head of the patient so that he can, after the laryngoscope blade is inserted in the patient's mouth, simultaneously grasp and raise the handle and then peer down into the throat of a patient. If the patient has a heavily muscled neck a great deal of strength is required to lift the laryngoscope to expand and expose the mouth and throat of a patient. In some cases a lone medical attendant simply does not have the strength necessary to lift the laryngoscope far enough to open the mouth and throat to view the larynx or to insert an endotracheal tube through the mouth and into the trachea of a patient. Insertion of an endotracheal tube is a standard precautionary measure because the tube permits a patient to breath if he vomits while receiving medical treatment.

A serious drawback is associated with the use of conventional L-shaped laryngeal speculums. After the blade of a conventional laryngoscope is properly positioned in the mouth of a patient and the handle is grasped and being lifted away from the patient, the pressure of the throat against the end of the laryngoscope blade adjacent the throat creates a torque force against the blade tip and causes the handle to rotate away from the medical attendant utilizing the laryngoscope. In order to properly lift the laryngoscope handle directly away from the patient a medical attendant must counteract this rotational torque force. The torque forces generated on lifting a laryngoscope can be substantial in a patient having a large neck and a medical attendant may not, in such cases, possess sufficient strength to lift the handle straight up in a direction parallel to the longitudinal axis of the handle, much less to counteract resultant torque forces. A common solution to this problem is for the attendant to position the end of the blade connected to the handle on the patient's upper incisor teeth and pull the handle toward himself, using the patient's teeth as a fulcrum about which to rotate the handle in a direction opposite the direction the handle is rotated by torque forces resulting when the handle is lifted away from the patient. This procedure has, as expected, resulted in numerous broken teeth and in personal injury lawsuits against various medical personnel.

Accordingly, it would be highly desirable to provide an improved laryngoscope which would not be subjected to resultant rotational forces when the handle of a laryngoscope is grasped and lifted directly away from a patient in a direction generally parallel to the longitudinal axis of the handle.

Therefore, it is a principal object of the invention to provide an improved laryngeal speculum.

Another object of the invention is to provide an improved laryngeal speculum having an elongate blade and an elongate handle connected to one end of the blade, the longitudinal axis of the handle being generally perpendicular to the longitudinal axis of the blade, and the handle being grasped and lifted away from the patient in a direction parallel to the longitudinal axis of the handle after the blade is inserted in the mouth of a patient to force the blade against tongue and throat areas of the patient to open and expand the same for viewing.

A further object of the invention is to provide an improved laryngeal speculum which can, after the blade thereof is inserted in the mouth of a patient, be grasped by the handle and lifted away from the patient without producing resultant torque forces which tend to rotate the laryngoscope handle in the hand of the medical attendant utilizing the laryngoscope.

Yet another object of the invention is to provide an improved laryngoscope handle which can be utilized with existing conventional laryngoscope blades.

Still a further object of the invention is to provide an improved laryngoscope blade which can be utilized with existing conventional laryngoscope handles.

These and other, further and more specific objects and advantages of the invention will be apparent to those skilled in the art from the following detailed description thereof, taken in conjunction with the drawings, in which:

FIG. 1 is a side elevational view of a conventional laryngeal speculum illustrating the mode of operation thereof;

FIG. 2 is a side elevation view of the best mode and presently preferred embodiment of the invention illustrating the mode of operation thereof;

FIG. 3 is a perspective view of the laryngeal speculum of FIG. 2 further illustrating construction details thereof; and FIG. 4 is a side view of a portion of the laryngoscope of FIG. 3 illustrating the electrical system thereof.

Briefly, in accordance with my invention, I provide an improved laryngeal speculum. The laryngeal speculum is utilized to examine the throat and larynx of a supine patient and to insert an endotracheal tube into the mouth and trachea of a patient so that the patient can breath if he vomits and the upper portion of the trachea is obstructed during administration of medical aide. The improved speculum includes an elongate blade having a longitudinal axis, a first end inserted into the mouth and throat of the patient during utilization of the speculum, a second end generally positioned outside the mouth of the patient during utilization of the speculum, and a central portion located along the length of the blade between the first and second ends; an elongate handle having a longitudinal axis generally perpendicular to the longitudinal axis of the blade, the user of the speculum grasping the handle and exerting a resultant lifting force parallel to the longitudinal axis of the handle in a direction away from the blade and from the patient to expand and open the mouth and throat of the patient for examination after the blade is inserted therein; and a neck having one end attached to the second end of the blade and another end attached to the handle, the neck being shaped, contoured and dimensioned such that the handle is generally positioned apart from the blade and over the central portion thereof and such that when the blade is positioned inside the mouth and throat of the patient the neck extends from the second end of the blade and around the chin of the patient to the handle and torque forces on the handle and blade are generally prevented from occurring when the lifting force is applied to said handle and the blade is forced upwardly against the tongue and anterior portions of the throat of the supine patient.

Turning now to the drawings, which depict the presently preferred embodiment and best mode of the invention for the purpose of illustrating the practice thereof and not by way of limitation of the scope of the invention, and in which identical reference characters correspond to like elements throughout the several views, FIG. 1 illustrates a conventional L-shaped laryngeal speculum generally identified by reference character 11 and comprising blade 12 fixedly, rigidly attached to handle 13. A medical attendant utilizing laryngoscope 11 stands or kneels behind head 14 of the patient, grasps handle 13 with his hand 15 and inserts blade 12 into the mouth of the patient to the position depicted in FIG. 1. The mouth and upper throat areas of the patient include tongue 17, lower teeth 18, upper teeth 20, uvulva 21, epiglottis 22, trachea 23, esophagus 19, soft palate 24 and hard palate 25. After blade 12 is inserted in the mouth of the patient handle 13 is lifted in a direction, indicated by arrow A in FIG. 1, away from the patient and generally parallel to the longitudinal axis of handle 13. As handle 13 is lifted, blade 12 is forced against tongue 17 and anterior portions of the throat to open and expose the mouth and throat of a patient for viewing. After handle 13 is lifted the desired distance the physician or medical attendant operating the laryngoscope looks into the mouth of the patient to examine the larynx and throat area or to insert an endotracheal tube through the mouth and into trachea 23 of the patient. The endotracheal tube permits the patient to breathe in the event the patient vomits while receiving medical care.

When handle 13 of the conventional laryngoscope of FIG. 1 is lifted in the direction of arrow A the throat and base of the tongue resist upward movement of end 27 of blade 12 and create torque forces represented by arrows B, C and D. These torque forces tend to rotate handle 13 away from the operator while laryngoscope 11 is being lifted in the direction of arrow A. Rotational forces B, C and D can, depending on the size and strength of the neck muscles of the patient, be substantial and require that the medical attendant operating the laryngoscope possess considerable strength in order to simultaneously lift the laryngoscope in the direction of arrow A and counteract torque forces B, C and D. If torque forces B, C and D are not offset, movement of blade point 27 in the throat can prevent the laryngoscope blade from properly exposing inner throat structures for viewing by a medical attendant.

FIGS. 2 to 4 illustrate the presently preferred embodiment and best mode of the invention, generally indicated by reference character 50 and including handle 30, arcuate neck 32 and elongate blade 33. Handle 30 and blade 33 have longitudinal axes 31, 34, respectively. Blade 33 includes free end 36 normally positioned inside the mouth and throat of the patient and end 37 positioned outside the mouth of the patient. Central portion 38 of blade 33 is, as indicated by arrows E, located between ends 36, 37 thereof. One end 40 of neck 32 is connected to end 37 of blade 33 while the other end 41 of neck 32 is attached to handle 30. Battery 42 in handle 30 provides electricity via wires 44 to power lightbulb 46. Lens 47 focuses light from blub 46 towards end 36 of blade 33. Cap 48 of handle 30 slides off of the end of handle 30 to allow battery 42 to be removed from handle 30. Neck 32 is shaped to extend from end 37 and around chin 49 of the patient to handle 30.

As illustrated in FIG. 2, when handle 30 of laryngoscope 50 is grasped and lifted away from the patient in a direction generally parallel to longitudinal axis 31 of handle 30, torque forces associated with conventional laryngoscope 11 are non-existant or greatly minimized. Positioning handle 30 over the central portion 38 of blade 33 effectively minimizes or eliminates such rotational forces during lifting of laryngoscope 50 away from the patient.

Many laryngoscopes in use today include a set of different sized blades which can each be quickly attached to and removed from the handle of the laryngoscope. (See for example U.S. Pat. No. 2,648,329 to Morch.) Such existing conventional laryngoscopes can be readily adapted for use in accordance with the invention by simply producing a neck 32 having an end 40 shaped to detachably receive an existing laryngoscope blade and having an end 41 shaped to be detachably received by an existing laryngoscope handle. For instance, if the laryngoscope described in Morch were being modified in accordance with the invention, end 40 of neck 32 (See FIGS. 2-4 herein) would be provided with headpiece 14 shown in FIG. 2 of Morch. The other end 41 of neck 32 (See FIGS. 2-4 herein) would be shaped like shank 64 of blade 66 in FIG. 2 of the Morch patent.

Similarly, in order to utilize the handles of existing laryngoscopes (assuming the existing blade could be detached therefrom), blade 33 and neck 32 in FIGS. 2-4 herein could be manufactured as a unitary piece adapted at end 41 of neck 32 to be readily connected to an existing laryngoscope handle.

In order to utilize the blades of an existing conventional laryngoscope (assuming the existing handle could be detached therefrom), handle 30 and neck 32 of FIGS. 2-4 herein could be produced as a unitary piece adapted at end 40 of neck 32 to receive an existing laryngoscope blade.

Having described my invention in such terms as to enable those skilled in the art to understand and practice it, and having identified the presently preferred embodiments and best mode thereof,

I claim:

1. A laryngeal speculum for
   examining the throat and larynx of a supine patient, and
   inserting an endotracheal tube into the mouth and trachea of a patient so that the patient can breath if the patient vomits and the trachea is obstructed during administration of medical aide,
said speculum including:
   (a) an elongate blade having
      (i) a longitudinal axis,
      (ii) a first end inserted into the mouth and throat of a patient during utilization of the laryngeal speculum,
      (iii) a second end generally positioned outside said mouth of the patient during utilization of said speculum, and
      (iv) a central portion located between said first and second ends along the longitudinal axis of the blade,
   (b) an elongate handle having a longitudinal axis generally perpendicularly disposed to said longitudinal axis of said blade, the user of said speculum grasping said handle and exerting a resultant lifting force parallel to said longitudinal axis of said handle in a direction away from said patient to expand and open the mouth and throat of the patient for examination after said blade is inserted therein; and
   (c) a neck having one end attached to said second end of said blade and another end attached to said handle, said neck being shaped, contoured and dimensioned such that
      (i) said handle is generally positioned apart from and over said central portion of said blade,
      (ii) when said blade is positioned inside the mouth and throat of said patient,
         said neck extends from said second end of said blade and around the chin of said patient to said handle, and
         torque forces on said handle and blade are generally prevented from occurring when said lifting force is applied to said handle and said blade is forced against the tongue and anterior portions of the throat of the supine patient.

2. The laryngeal speculum of claim 1 wherein said neck, handle and blade are substantially rigid.

* * * * *